United States Patent [19]

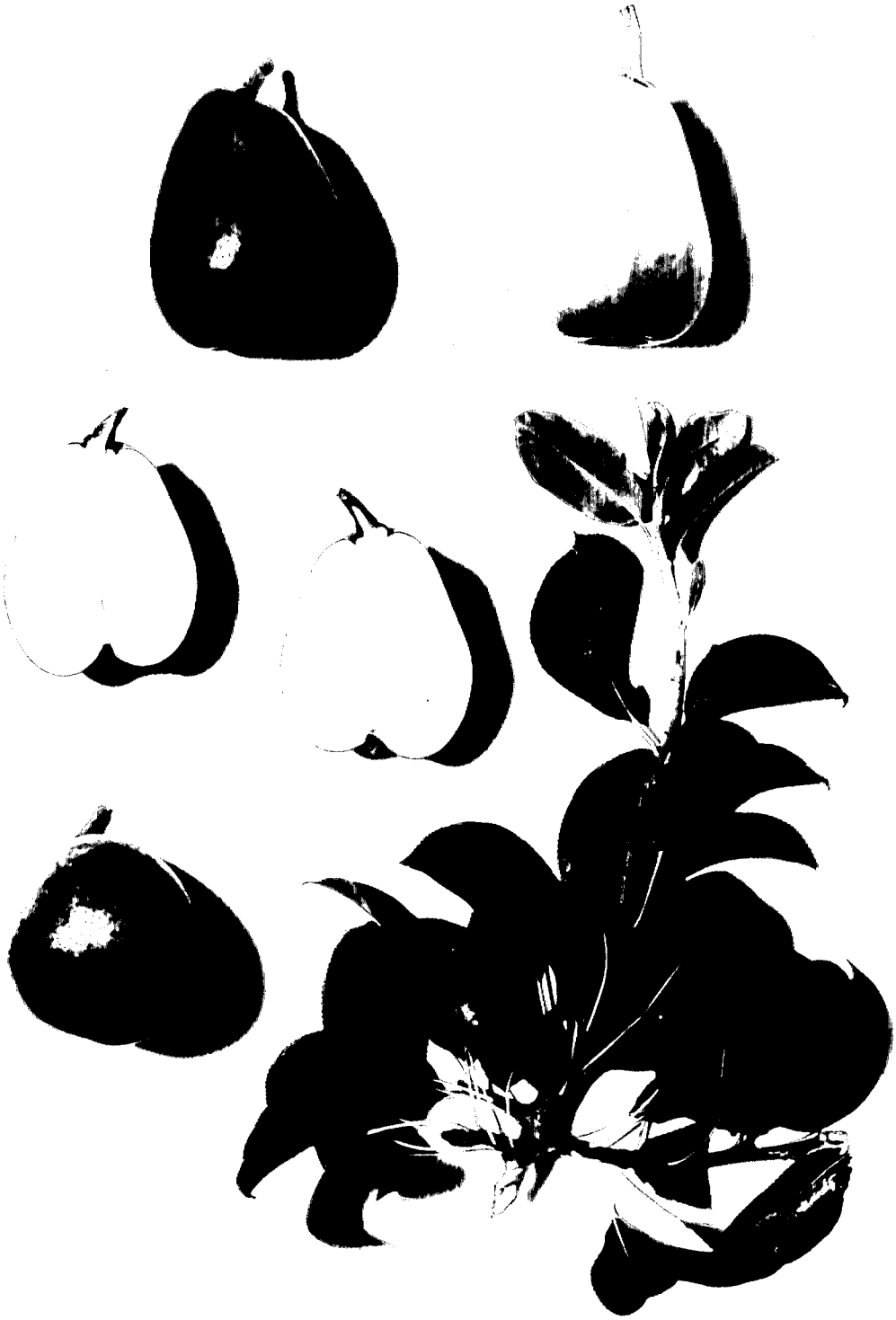

Petersen

[11] Patent Number: Plant 5,570

[45] Date of Patent: Oct. 8, 1985

[54] PEAR TREE "SAN JOAQUIN"

[76] Inventor: Robert E. Petersen, 11597 S. Academy, Selma, Calif. 93662

[21] Appl. No.: 583,330

[22] Filed: Feb. 24, 1984

[51] Int. Cl.[4] ..... A01H 5/03
[52] U.S. Cl. ..... Plt./36
[58] Field of Search ..... Plt./36

*Primary Examiner*—Robert E. Bagwill

*Attorney, Agent, or Firm*—Huebner & Worrel

[57] ABSTRACT

A pear tree, denominated "San Joaquin", having fruit ripening for picking about June 11 and to full maturity about June 20, at early maturity having deep green ground color with a brown-red blush in a partially solid, partially striped pattern, the ground color lightening to reach a bright yellow at full maturity and the blush a cherry red.

1 Drawing Figure

BACKGROUND OF THE VARIETY

The present invention relates to a new and distinct variety of pear tree, denominated "San Joaquin", broadly characterized by its early maturing fruit ripening in the San Joaquin Valley of Calif. for picking about June 11 and to full maturity about June 20 and being further characterized by the fruit having a distinctive turbinate to slightly ovate-pyriform and having at full maturity a bright yellow ground color with a cherry red blush frequently occurring in a striped pattern with some solid areas of color.

Early ripening tree fruit has a considerable commercial advantage over the later ripening varieties. In the case of pear trees, this market advantage also prevails. The unpatented Precoce Morettini pear tree is the earliest ripening commercial variety of pear tree with fruit of green-yellow coloration grown in California and its fruit enjoys goods market acceptance. The Starkrimson pear tree of U.S. Plant Pat. No. 1,095 is the earliest ripening commercial variety of pear tree with fruit of red coloration grown in California and its fruit also has strong market value. In the San Joaquin Valley of Calif. the Precoce Morettini pear tree ripens about June 25 and the Starkrimson pear tree about July 11. The pear tree of the present invention is distinct from these prior varieties as well as other known varieties in that it produces fruit which ripens for commercial harvesting about June 11 and has at such commercial maturity a deep green ground color with a red blush lightening at full maturity to a bright yellow ground color with a cherry red blush.

ORIGIN AND ASEXUAL REPRODUCTION OF THE NEW VARIETY

The new variety of pear tree of the present invention was discovered by myself in June of 1979 and is a newly found seedling of unknown parentage discovered in a cultivated family orchard not in commercial use at Lincoln and McCall Avenues, Del Rey, Calif. in the United States of America. The orchard at that time belonged to a Mr. Jim Swanson. The new variety's distinctive characteristics were discovered by me at that time. Wood of the newly found seedling was used asexually to reproduce the new variety at my direction by budding pear rootstock. The resulting trees of the new variety are located in an orchard planting on my property located at Academy and Rose Avenues, Selma, Calif. in the United States of America. The seedlings of the new variety and the parent tree were observed over several growing seasons and the fruit and tree characteristics resulting from such asexual reproduction proved to be identical to those of the original seedling of the new variety.

SUMMARY OF THE NEW VARIETY

The instant variety of pear tree is characterized by its fruit which ripens for picking about June 11 and reaches full maturity about June 20 in the San Joaquin Valley of Calif. and which is at full maturity of turbinate to slightly ovate-pyriform shape having a bright yellow skin with cherry red blush usually occurring in a striped pattern with some solid areas of blush.

BRIEF DESCRIPTION OF THE DRAWING

The accompanying drawing is a color photograph of five mature fruit of the variety of the present invention, a first in the upper left hand corner of the photograph positioned to show the side thereof and showing coloration characteristic of the fruit at commercial maturity about June 11, a second in the upper right hand corner of the photograph positioned to show the side thereof and showing coloration characteristic of the fruit at full maturity about June 20, a third and a fourth left of center in the photograph each sliced in a plane coincident with its longitudinal axis with the seeds left in place and a fifth near the lower left hand corner of the photograph positioned to show the basin end. A representative twig is also shown near the lower right hand corner of the photograph with characteristic leaves.

DETAILED DESCRIPTION

Referring more specifically to the pomological details of this new and distinct variety of pear tree, the following characteristics were observed under the ecological conditions prevailing at an orchard planting at Academy and Rose Avenues, Selma, Calif. in the United States of America. All major color code plate identifications are by reference to the *Dictionary of Color;* Maerz and Paul, published in 1950.

TREE

Size: Medium to large.

Figure: Very upright and tall when young, spreading with age and crop.

Productivity: Good.

Regularity of bearing: Good.

Trunk: Medium in size with a medium to smooth surface texture. Older bark has numerous lenticels and is greyish. Color (14-A-3).

Branches: Medium in size and surface texture. Mature one year old shoots have numerous lenticels and are brown. Color (15-E-7). Young shoots have fine pubescence and are green. Color (19-I-6).

9 Leaves: Medium size and moderately thick with mature leaves being somewhat leathery. Measurements given hereinafter are of average leaves at midpoint of vigorously growing shoots.

*Length.*—Average length, exclusive of petiole, 76 mm.

*Width.*—Average width 47 mm.

*Shape.*—Oval with mucronate tip often slightly twisted.

*Margin.*—Broadly crenate, usually straight and only occasionally undulate.

*Color and character.*—Upper leaf surface dark green (23-L-9) and relatively smooth. Lower leaf surface light green (20-E-5) with fine pubescence especially on immature leaves. Upper midvein light green (20-H-3) with light pubescence and irregularly studded with short coarse brown hairs.

*Petiole.*—Variable in length, moderately long from 14 to 30 mm. Most commonly averaging 18 to 22 mm. Slender, average thickness 1 to 1.5 mm. Light green-yellow. Color (18-H-4).

*Stipules.*—Two near base of petiole, light green. Color (18-T-6). Average length 10 to 11 mm. and often but not always deciduous on mature leaves.

Flower buds: Medium to large in size. Hardy under growing conditions prevailing in California. Plump, 5 to 6 mm. long.

*Pubescent.*—Bud scales covered with short light brown hairs. Color (15-J-11).

Flowers:

*Date of bloom.*—Mid March, Flower resembles flower of the Bartlett pear tree.

FRUIT

Maturity: Reached in the San Joaquin Valley of Calif. for picking June 11 to June 16 with full maturity reached on June 20. Description hereinafter given for fruit at full maturity.

Size: Uniform. Medium to large size. Average axial length 75 to 78 mm. Average diameter 67 to 68 mm.

Form: Turbinate to slightly ovate-pyriform. Usually quite symmetrical, but sometimes elliptical in plane transverse to longitudinal axis.

*Stem.*—Medium to moderately long with medium thickness. Average length 30 to 35 mm. Thick near point of attachment to fruit, averaging 6 to 8 mm., and more slender near point of attachment to branch, averaging 4 to 5 mm. Stem frequently oblique to longitudinal axis of fruit. Brownish color (13-F-8).

*Stem cavity.*—Shallow line at stem end frequently lipped on one side.

*Calyx.*—Small, persistent and usually closed.

*Calyx lobes.*—Frequently united at base and often partially recurved.

*Calyx tube.*—Moderately small with a broad, urn shape.

*Stamens.*—Median in position within calyx tube.

*Basin.*—Medium to shallow in depth. Medium to slightly narrow in width, averaging 15 to 17 mm. Sides smoothly rounded from shoulder and surface moderately furrowed. Basin is usually symmetrical.

Skin:

*Thickness.*—Moderately thick.

*Surface.*—Smooth and waxy with a light bloom.

*Color.*—At picking or commercial maturity, ground color is green (21-I-8) with brown-red blush color (7-J-10) at times covering 30 to 50 percent of fruit surface. Blush usually occurs in a striped pattern with some solid areas of color. Upon reaching full maturity, ground color changes to a bright yellow (10-K-3) with blush color changing to a cherry red (4-K-11).

*Dots.*—Numerous, medium sized and areolar with dark green halo when fruit slightly immature which disappears as fruit ripens.

Flesh:

*Color.*—White.

*Juice.*—Juicy when ripe.

*Texture.*—Medium, slightly grainy.

*Flavor.*—Sweet and well balanced.

*Aroma.*—Moderate and pleasant.

*Core.*—Small in size and distant from stem in position. Carpel cells are closed. Core lines meeting above base.

*Carpels.*—Oblong in shape, emarginate, axile, surface character is smooth.

*Seed.*—Fertile seed not present in fruit from this location. Fruit apparently set parthenocarpically.

Quality: Good for early season of maturity.

Use: Local and long distance fresh market.

*Keeping quality.*—Average for date of maturity. Short storage life in comparison to mid-season varieties.

*Shipping quality.*—Average.

*Insect and disease resistance.*—Average for species.

Although the new variety of pear tree possesses the described characteristics as a result of the growing conditions in Fresno County, Calif., in the Central portion of the San Joaquin Valley in the United States of America, it is to be understood that variations of the usual magnitude and characteristics incident to growing conditions, fertilization, pruning, pest control and other horticultural practices are to be expected.

Having thus described and illustrated my new variety of pear tree, what is claimed as new and desired to be secured by Letters Patent is:

1. A new and distinct variety of pear tree substantially as illustrated and described and which is characterized by its fruit being early ripening occurring for picking about June 11 and reaching full maturity about June 20, by the color of the fruit having about June 11 a deep green ground color and a brown-red blush extending in a partially solid, partially striped pattern over 30 to 60 percent of the skin surface and at full maturity the ground color lightening to bright yellow and the blush to cherry red.

* * * * *

UNITED STATES PATENT AND TRADEMARK OFFICE

CERTIFICATE OF CORRECTION

PATENT NO. : PP 5,570

DATED : October 8, 1985

INVENTOR(S) : Robert E. Petersen

It is certified that error appears in the above-identified patent and that said Letters Patent is hereby corrected as shown below:

Column 3, line 34, delete "(18-T-6)" and substitute

---(18-I-6)---.

Signed and Sealed this

*Twelfth* Day of *August 1986*

[SEAL]

*Attest:*

DONALD J. QUIGG

*Attesting Officer*

*Commissioner of Patents and Trademarks*